United States Patent
Iger

(10) Patent No.: US 9,463,308 B2
(45) Date of Patent: Oct. 11, 2016

(54) DEVICE FOR PRESSURE ENHANCED FRACTIONAL TREATMENT AND DRUG DELIVERY

(71) Applicant: LUMENIS LTD., Yokneam Ilit (IL)

(72) Inventor: Yoni Iger, Haifa (IL)

(73) Assignee: LUMENIS LTD., Yokneam Lilt (IL)

( * ) Notice: Subject to any disclaimer, the term of this patent is extended or adjusted under 35 U.S.C. 154(b) by 161 days.

(21) Appl. No.: 14/354,275

(22) PCT Filed: Oct. 30, 2012

(86) PCT No.: PCT/IB2012/056023
§ 371 (c)(1),
(2) Date: Apr. 25, 2014

(87) PCT Pub. No.: WO2013/076602
PCT Pub. Date: May 30, 2013

(65) Prior Publication Data
US 2014/0276370 A1    Sep. 18, 2014

Related U.S. Application Data

(60) Provisional application No. 61/554,465, filed on Nov. 1, 2011.

(51) Int. Cl.
*A61B 17/20* (2006.01)
*A61M 37/00* (2006.01)
*A61N 7/00* (2006.01)
*A61B 17/00* (2006.01)
*A61B 18/20* (2006.01)
*A61B 18/00* (2006.01)

(52) U.S. Cl.
CPC ......... *A61M 37/0092* (2013.01); *A61M 37/00* (2013.01); *A61N 7/00* (2013.01); *A61B 18/203* (2013.01); *A61B 2017/00747* (2013.01); *A61B 2017/00765* (2013.01); *A61B 2018/0047* (2013.01); *A61M 37/0015* (2013.01); *A61M 2037/0007* (2013.01); *A61N 2007/0034* (2013.01); *A61N 2007/0039* (2013.01)

(58) Field of Classification Search
CPC ................ A61M 2037/0007; A61M 37/0092; A61M 37/00; A61M 37/0015; A61B 18/203; A61B 2017/00747; A61B 2017/00765; A61B 2018/0047; A61N 2007/0034; A61N 2007/0039; A61N 7/00
See application file for complete search history.

(56) References Cited

U.S. PATENT DOCUMENTS

| | | |
|---|---|---|
| 2002/0038101 A1 | 3/2002 | Avrahami et al. |
| 2004/0024348 A1 | 2/2004 | Redding |

(Continued)

*Primary Examiner* — Rebecca E Eisenberg
(74) *Attorney, Agent, or Firm* — Isus Intellectual Property PLL

(57) ABSTRACT

Disclosed herein is a method of fractional treatment of tissue, the method comprising: creating at least one micro hole in a target tissue; and either a) applying pressure on said target tissue to decrease the patency of said at least one micro hole; administering material and/or fluid and/or drug onto said target tissue; releasing said applied pressure on said target tissue to increase the patency of said at least one micro hole; and propelling said material and/or fluid and/or drug into said at least one micro hole; or b) administering material and/or fluid and/or drug onto said target tissue under sub-atmospheric pressure conditions, the patency of said at least one micro hole being decreased; increasing the atmospheric pressure to atmospheric or above atmospheric conditions to thereby increase the patency of said at least one micro hole; and propelling said material and/or fluid/and/or drug into said at least one micro hole.

16 Claims, 4 Drawing Sheets

(56) References Cited

U.S. PATENT DOCUMENTS

| | | |
|---|---|---|
| 2004/0106904 A1 | 6/2004 | Gonnelli et al. |
| 2006/0004347 A1 | 1/2006 | Altshuler et al. |
| 2008/0208179 A1* | 8/2008 | Chan .................. A61B 18/203 606/9 |
| 2010/0004582 A1 | 1/2010 | Bragagna et al. |
| 2011/0245728 A1 | 10/2011 | Eppstein et al. |

* cited by examiner

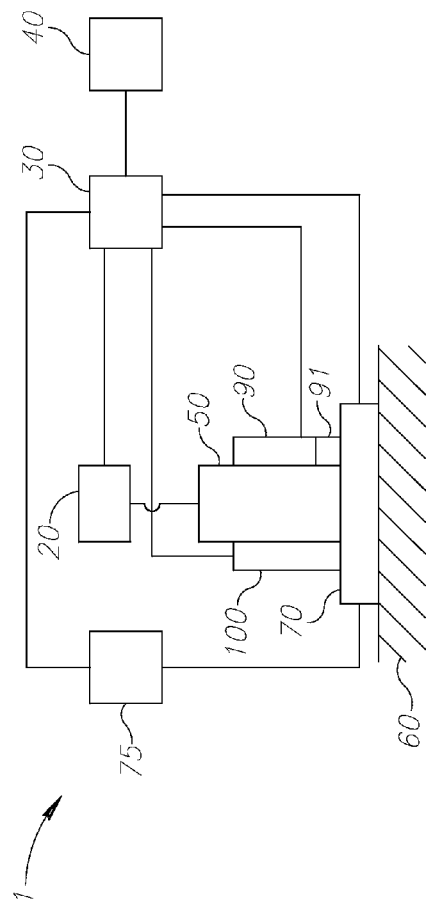
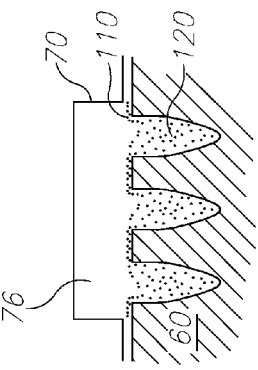
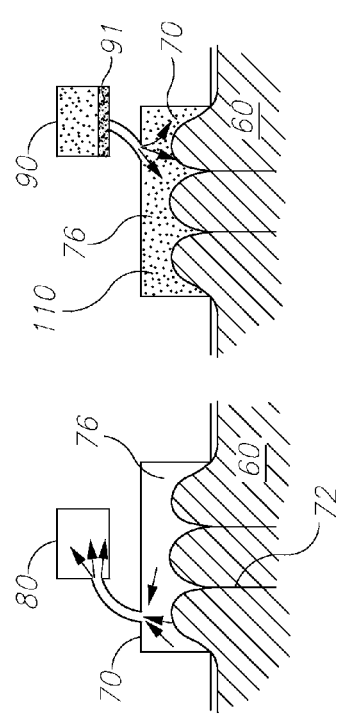
Figure 1A
Figure 1B
Figure 1C
Figure 1D
Figure 1E

DEVICE FOR PRESSURE ENHANCED FRACTIONAL TREATMENT AND DRUG DELIVERY

TECHNICAL FIELD

The present invention relates to fractional tissue treatment and more particularly, to pressure enhanced fractional treatment and drug delivery devices.

BACKGROUND OF THE INVENTION

Ablative fractional laser devices have gained acceptance as a preferred method for skin rejuvenation. Notable improvements in facial rhytides, photodamage, acne scarring, skin laxity, to name but a few conditions, are now well known. This type of invasive fractional tissue treatment is based on micro holes created (or "drilled") in a target tissue using an energy source, such as a laser. Other types of energy sources are known to be effective in producing micro holes. Among these sources are: lasers, as already mentioned above, micro needles, micro electrodes, cryogenically cooled micro tips, ultrasound, radio-frequency and others. Each individual hole is surrounded by non-damaged tissue. Holes density, i.e. the number of holes per unit of area, as well as hole-depth and hole-surrounding coagulated tissue, within the target tissue may all vary according to the treatment protocol and clinical objectives.

Although it is relatively straight forward to create or "drill" such holes or micro-holes for fluid communication, the micro holes tend to collapse after the ablation or there is fluid oozing out the micro holes. Therefore, in any of the prior art methods it is still a great challenge to control the micro hole dimension or patency during its creation and thereafter.

It is, therefore, an aim of the present invention to provide a method and a device to alleviate some of the problems of the prior art methods.

BRIEF SUMMARY

One aspect of the invention provides a method of fractional treatment of tissue. The method comprising: creating at least one micro hole in a target tissue; and either a) applying pressure on said target tissue to decrease the patency of said at least one micro hole; administering material and/or fluid and/or drug onto said target tissue; releasing said applied pressure on said target tissue to increase the patency of said at least one micro hole; and propelling said material and/or fluid and/or drug into said at least one micro hole; or b) administering material and/or fluid and/or drug onto said target tissue under sub-atmospheric pressure conditions, the patency of said at least one micro hole being decreased; increasing the atmospheric pressure to atmospheric or above atmospheric conditions to thereby increase the patency of said at least one micro hole; and propelling said material and/or fluid/and/or drug into said at least one micro hole.

Another aspect of the invention provides a device for fractional treatment of tissue, device for fractional treatment of tissue, said device comprising: an energy source, wherein said energy source is configured to create at least one micro hole in a target tissue; a pressure source, wherein said pressure source is configured to exert and release pressure on said target tissue; a reservoir, wherein said reservoir is configured to contain material and/or fluid and/or drug and controllably release said material and/or fluid and/or drug onto said target tissue; and a controller, wherein said controller is configured to control the activation of at least one of said energy source, said pressure source and said reservoir.

There is also provided a process or method for ultrasound enhanced fractional treatment of tissue, the process or method comprising: drilling or creating at least one micro hole in a target tissue; allowing a fluid secreted by the target tissue adjacent to said at least one hole to penetrate into said at least one hole; applying ultrasound energy on said target tissue and secreted fluid, causing the formation of at least one cavitation bubble in said secreted fluid; and controlling said at least one hole patency by controlling said applied ultrasound characteristics affecting at least one of the following: bubble average size; bubbles density; bubble average formation pace; bubble average growing pace; bubble average shrinking pace; and bubble exploding pace.

A process or method for ultrasound enhanced fractional treatment of tissue, may comprise: drilling or creating at least one hole in a target tissue; administering a fluid on said target tissue and allowing said administered fluid to at least partially penetrate said at least one hole; applying ultrasound energy on said target tissue and said administered fluid causing the formation of at least one cavitation bubble in said administered fluid; and controlling said at least one hole patency by controlling said applied ultrasound characteristics affecting at least one of the following: bubble average size; bubbles density; bubble average formation pace; bubble average growing pace; bubble average shrinking pace; and bubble exploding pace.

In the process, the ultrasound energy is applied approximately perpendicular to the surface of said target tissue.

Preferably the ultrasound energy is applied to create surface waves which are approximately parallel to said surface of said target tissue.

The process may further comprise administering material onto said target tissue.

In the process the administering of the material may further comprise administering a fluid.

In the process, the administering of the fluid may further comprise administering a drug.

In the process, the administering fluid may further comprise administering a cosmetic material.

The process may further comprise applying ultrasound energy so that at least one hole patency is changing over time and the administered material penetration pace into the at least one hole is increased.

The process may further comprise applying an ultrasound energy to cause cavitation of at least one bubble.

The process may further comprise controlling the at least one bubble cavitation pace.

The process may further comprise controlling the damage of the target tissue.

The process may further comprise administering of an abrasive material.

The process may further comprise applying ultrasound, electrical or optical energy to activate the abrasive material or material to be delivered.

The abrasive material may be activated by the energy source.

An sonodynamic therapy process for ultrasound enhanced fractional treatment of tissue, may comprise: drilling or creating at least one hole in a target tissue; administering a fluid onto the target tissue and allowing the administered fluid to at least partially penetrate the at least one hole; and applying ultrasound energy on said target tissue.

In the above process, the administered fluid may comprise a sonosensitizable agent capable of undergoing an exothermic reaction. In this embodiment, the fluid comprises submicron particles which serve as cavitation grains. In this embodiment the fluid may comprise a silica derivative.

Alternatively the administered fluid may comprise an active ingredient, for example Amino Levulenic acid or any other photo sensitizer. In this embodiment, the fluid causes oxidative impact in the hole and/or on the hole walls, thus increasing the patency of the hole.

A therapy process may be a combination of the application of pressure (as detailed in the first method above) and further the application of ultrasound energy for further enhancement of the fractional treatment.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout several views.

FIG. 1A illustrates one conceptual configuration of the present invention.

FIG. 1B illustrates an embodiment in which the energy delivery mechanism, the pressure applicator and the pressure applicator aperture are placed over a target tissue.

FIG. 1C illustrates one aspect of the present invention, wherein the pressure applicator applies negative pressure over the tissue causing the tissue to be sucked into the aperture and hole's patency to be decreased.

FIG. 1D illustrates another embodiment of the present invention, once the patency of the hole is reduced or decreased, the material dispensing element releases material into the pressure applicator aperture.

FIG. 1E depicts a further embodiment of the present invention.

Figure 2B:
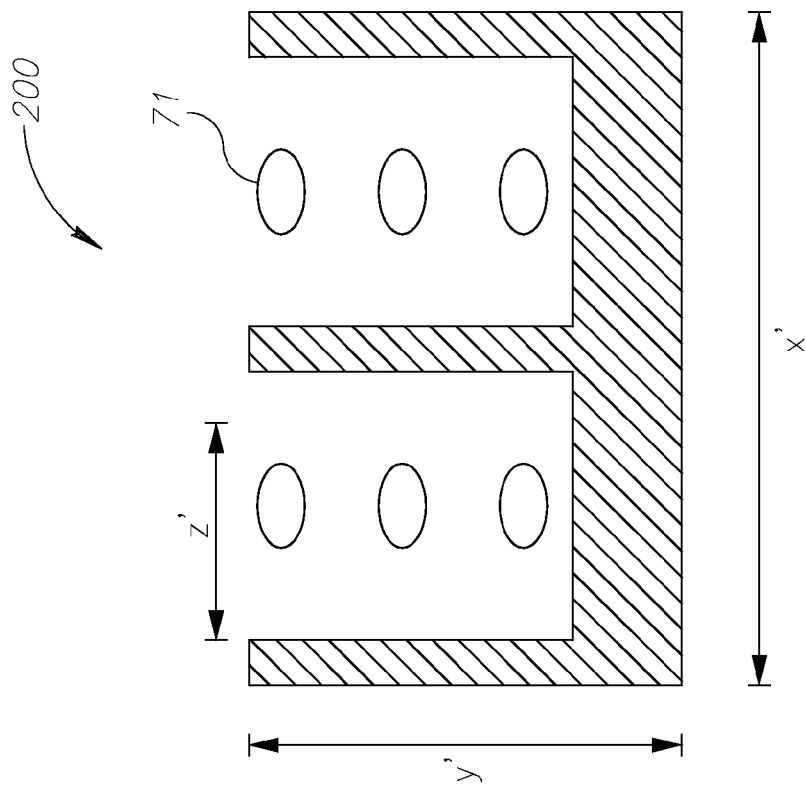
FIGS. 2A and 2B illustrate one conceptual configuration of the mechanical grid according to the present invention.

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "laser", as used herein, refers to any type of laser for example: solid state (e.g. Neodymium YAG, Erbium YAG, Holmium YAG, Thulium or Alexandrite); diode (e.g. in various wavelengths, such as in the range 532-1600 nm); gas (e.g. $CO_2$, Argon); or fiber laser (e.g. Neodymium, Erbium, Holmium, Thulium or Alexandrite). Furthermore, laser beams referred to in the application may be: continuous pulsed; long pulsed, short pulsed, Q-switched pulse; or any other temporal pattern.

The term "treatment beam", as used, herein, refers to an intense laser beam transferred through an optical fiber or through air to treat a target tissue. For example, the treatment beam may be a pulsed laser beam or any other laser beam as defined above. The treatment may be ablative or non-ablative, as determined by the beam intensity in respect to a tissue ablation threshold.

The term "fractional treatment", as used herein, refers to a treatment of a target tissue or organ in which at least one treatment point, or rather, a micro hole is created in the tissue and is surrounded by a non-treated tissue. On a target tissue, one or more treatment points may be created in a variety of sizes, depths, patterns and densities. Fractional treatment may be invasive, non-invasive or any combination of the two.

The term "energy source", as used, herein, refers to any energy source which may create fractional treatment. As non limiting examples for such energy sources are: laser; non-coherent light sources; radio frequency generators; microwave generators; cryogenically cooled material; ultrasound etc.

The term "patency", as used herein, means the state or quality of being open, expanded, or unblocked.

The term "cavitation", as used herein, is the formation and then immediate implosion or explosion of cavities in a liquid—i.e. small liquid-free zones ("bubbles")—that are the consequence of forces acting upon the liquid. This usually occurs when a liquid is subjected to rapid changes of pressure that cause the formation of cavities where and when the pressure is relatively low.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1A illustrates a high level conceptual configuration of one embodiment of the present invention. System 1 includes an energy source 20 which is controlled by control unit 30. Control unit 30 has a user interface 40 which allows the user, among other things, to set the working parameters of the system for a chosen treatment. Energy delivery mechanism 50 is functionally connected to energy source 20 and is configured to deliver treatment energy from the energy source 20 to the target tissue 60. Different energy sources may require different energy delivery mechanisms. Non limiting examples for energy delivery mechanisms are: optical fiber; free beam scanner; beam splitters; light guides; micro needles; micro electrodes; cryogenically cooled tips; micro transducers etc. All of these systems produce micro holes in the tissue that is being treated. Any of these systems, or a combination thereof, may be used in the present invention.

The energy delivery mechanism 50 is configured to be placed on or above the target tissue 60 and to functionally deliver energy from energy source 20 onto the target tissue 60 to fractionally treat the tissue. That is, to create micro holes 71 in the tissue that is to be treated, as shown in FIG. 1B. As mentioned above the energy source 20 may comprise any of the systems described above, or a combination thereof.

A pressure applicator 70 contacts the target tissue 60. The pressure applicator 70 is in fluid communication with a pressure source 75. The pressure source 75 may also be controlled by control unit 30, or it may be controlled by a separate controller. It is the application of pressure onto the micro hole which allows the patency of the micro hole to be controlled. Energy delivery mechanism 50 and pressure applicator 70 are configured to work independently and simultaneously on the same target tissue 60 so that different pressure levels can be applied on the target tissue before, during or after energy delivery mechanism 50 delivers energy to the target tissue 60.

In another embodiment of the present invention, the pressure applicator can be a mechanical instrument which is configured to fold the target tissue or to apply lateral pressure which tends to close the at least one hole. Such a mechanical instrument may be configured in a scissors like or tweezers like configuration. According to another embodiment of the mechanical pressure applicator a temperature conditioning mechanism may be integrated in or coupled to the instrument. A temperature conditioning mechanism may cool or heat the target tissue in order to affect its mechanical or chemo-kinetic of the target tissue.

In one embodiment of the present invention the energy source 20 is a light source and energy delivery mechanism 50 may be, for example, a scanner, a fiber, a light guide or a beam splitter. In this configuration, pressure applicator 70 may be a transparent material for the treatment beam wavelength with an aperture to contact the target tissue 60. The aperture may apply positive or negative pressure on the target tissue.

Alternatively, the administering of the fluid takes place under sub-atmospheric pressure, thereafter the treatment tissue is subject to atmospheric or above atmospheric pressure, thereby increasing the patency of the hole or holes.

In yet another embodiment of the present invention the energy source may be an array of micro needles which are configured to reach the target tissue 60 through pressure applicator 70 while still allowing, simultaneously or consequently, the pressure applicator to apply negative or positive pressure on the target tissue 60, before, during or after the fractional treatment.

In yet another embodiment an array of cryogenically cooled tips may be applied on the target tissue through pressure applicator 70 to create the micro holes. In yet a further embodiment of the present invention an array of micro transducers create the micro holes in the target tissue.

In the present invention, the system may comprise a reservoir 90 configured to hold at least one material. The material may be a cosmetic fluid, such as anti-oxidant, hyaluronic acid or collagen, or other fluid such as a drug, which may be, for instance, Botox™, used either as a cosmetic treatment or medical treatment. Reservoir 90 is in fluid communication with the aperture of pressure applicator 76 through material dispensing element 91. The material dispensing element 91 may also be controlled by control unit 30. The material dispensing element may be micro needles, nozzles or other such delivery system. Control unit 30 may also control reservoir 90 and monitor its content through at least one sensor.

In yet another embodiment of the present invention, an excess fluid removal unit 100 may be in fluid communication with pressure applicator aperture 76 of FIG. 1B. In conditions of excess fluid accumulated in the pressure applicator aperture 76, whether due to over flow from material reservoir 90 or spontaneous fluid secretion from the target tissue 60 or holes 71, excess material removal unit will remove excess fluid. This is particularly useful when, for instance, the treatment is used for the removal of acne spots or boils, where fluid may accumulate in the target treatment area. Unit 100 may be controlled by control unit 30, or have a separate controller. A fluid sensor in the pressure applicator may be controlled by control unit 30, which may activate excess material removal unit when excess fluid is detected. A tissue temperature conditioning unit may be configured to affect spontaneous fluid secretion. According to one embodiment of the present invention the tissue temperature conditioning unit may cool the tissue in order to reduce spontaneous secretion.

FIG. 1B illustrates an embodiment of the present invention, in which the energy delivery mechanism 50, pressure applicator 70 and pressure applicator aperture 76 are placed over the target tissue 60. In this embodiment, the system has delivered fractional treatment to underneath the target tissue 60 to create micro holes 71. The pressure applicator maintains aperture 76 in a condition which allows micro holes 71 to be relatively open. In one embodiment, the pressure applicator 70 may comprise of a cooling element which reduces the target tissue temperature so that the module of elasticity of the target tissue is effectively reduced, and therefore, the micro holes do not tend to collapse. Alternatively, mechanical support, for instance, by means of a grid, may be provided. In yet another embodiment of the present invention, the pressure applicator may maintain a certain degree of positive pressure over the tissue so that the pressure inside the holes is bigger than the pressure applied by the walls of the hole and therefore maintain its patency. That is, maintain the opening to the size required, such that the injection of the fluid is facilitated.

Referring now to FIG. 1C, in one embodiment of the present invention, the pressure applicator applies negative pressure over the tissue, causing the tissue to be sucked and inserted into aperture 76 and holes 72 patency to be decreased. A negative pressure source 80 may be in fluid communication with pressure applicator aperture 76. This treatment may be useful also for the removal of oozing fluids from ablated holes, as well as for the treatment of such conditions as acne or boils, where fluid exists and further builds up in the target tissue.

In yet another embodiment of the present invention, the target tissue 60 may be pinched by pressure applicator with positive pressure from the sides causing similar effect of reducing holes patency. The pressure inside and outside the holes determines the degree of patency of the micro holes. As the pressure can be finely controlled, the present invention is amenable for use in a variety of tissue conditions.

Referring now to FIG. 1D, in another embodiment of the present invention, once holes patency is reduced, material dispensing element 91 releases material into the pressure applicator aperture 76 so that at least part of the target tissue surface is covered by the material 110. The material 110 has adequate viscosity level to be effectively dispensed by dispensing element 91 and has adequate wetting properties to cover most of the target tissue surface. The material may incorporate a therapeutic material or cosmetic material or a mix of different materials to achieve a certain physiological effect. The material may also be an inert material, for example, micro-fillers.

Referring now to FIG. 1E, in yet another embodiment of the present invention, once the negative pressure has been released while the target tissue surface is covered, at least partially, by the administered material 110, the tissue returns approximately to its original position, hole patency is increased and as a result material 110 is sucked and pushed into the hole volume 120. This has the advantage that, for example, when a cosmetic material is inserted into the target tissue, for example, collagen or Botox™, the material is sucked in deeply through capillary action and is later diffused and absorbed by the surrounding tissue.

In yet another embodiment, hole patency may be increased, for example, by cooling the tissue, or stretching the tissue, by the pressure applicator 70 or by an adjustable grid.

An increase in hole patency once the material has been administered onto the tissue will create a force which sucks and pushes the material into the hole volume so that any active material will now have direct communication with inner layers of the tissue and through a larger surface area.

In yet another embodiment of the present invention, an adjustable grid may be applied on the target tissue which may stabilize, stretch or compress the tissue in such a way that the hole patency may be manipulated (changed or kept the same, as required). The adjustable grid may comprise of a stretchable, flexible material, so that the micro holes are further apart, or a pre-stretched grid which is released in tension so that the distance between the micro holes is decreased. The grid may also be used to stabilize the target tissue. This has the advantage that an exact doze of fluid can be administered to the target tissue.

Figure 2A:
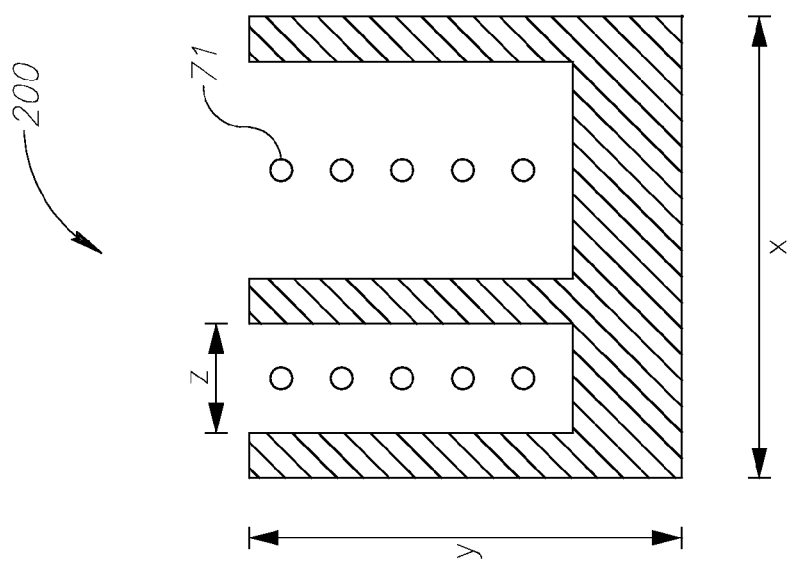

Referring now to FIGS. 2A and 2B which conceptually illustrates one embodiment of the adjustable grid 200. The adjustable grid 200 has at least a length dimension x, a width dimension y and a spacing dimension z. The grid is configured to be placed and be fixated on the target tissue 60 while fractional treatment is delivered onto the tissue through the grid spacing. In order to increase the hole patency at least one dimension of the grid may be adjustable as shown in FIG. 2B. Here the micro holes 71 are increased in size by stretching the grid if the grid is made of a flexible material. Different grid layouts and adjustable dimensions may be applied to change the micro hole patency before, during or after fractional treatment is applied or the material has been administered. In one embodiment of the present invention, the grid is made of a rigid material such as a medical grade plastic and is fixated onto the tissue by a medical grade sticker. In yet another embodiment, the grid is made of a metal. In another embodiment the grid is only a partial grid. Changes of hole patency create suction forces which accelerate material penetration into the hole volume and overcome friction and capillary forces which may otherwise prevent the material from penetrating the hole. This is especially true for some fluids such as medical fluids.

Figure 3:
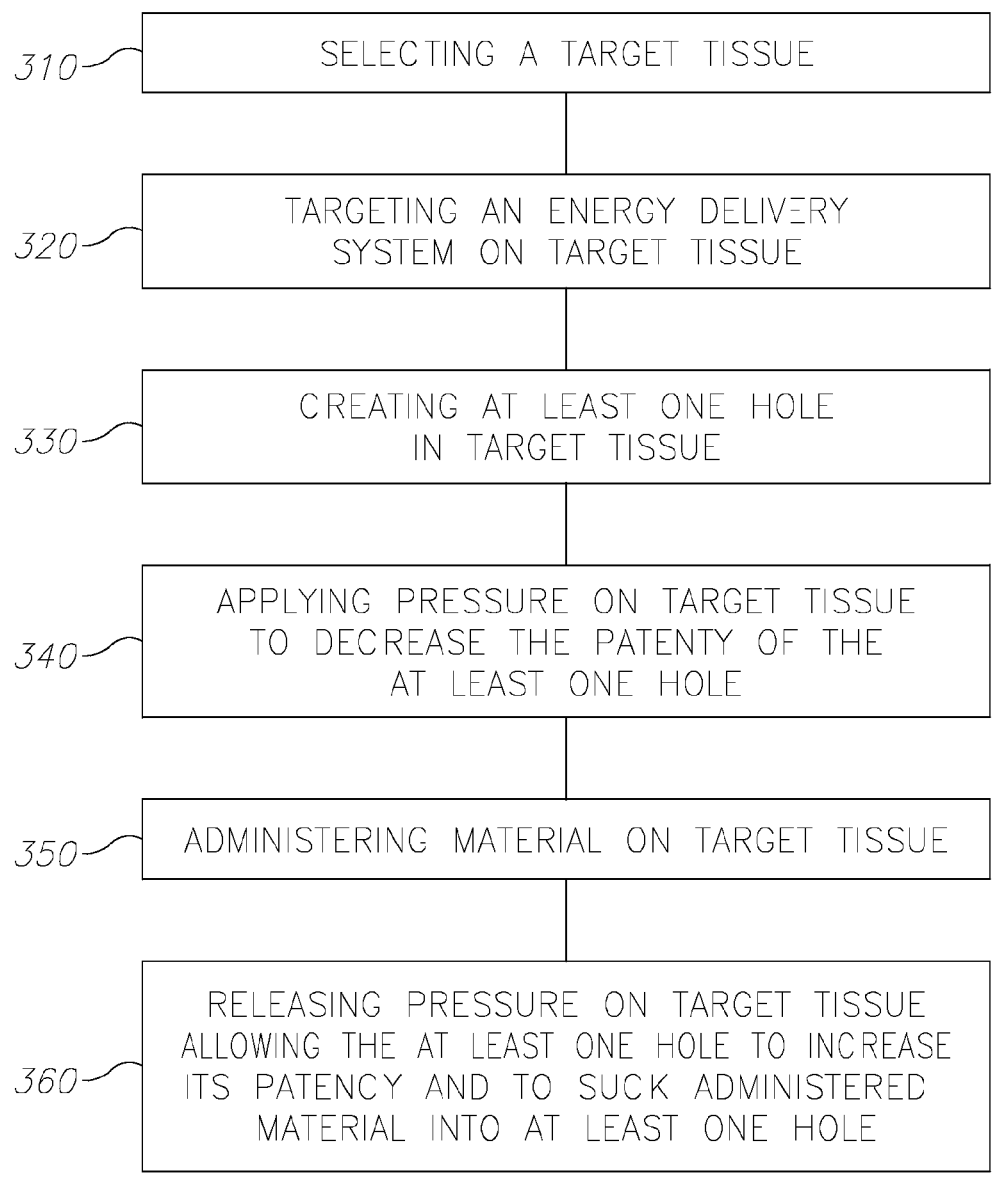
FIG. 3 schematically illustrates a high level flowchart according to some embodiments of the invention.

Referring now to FIG. 3, a high level flowchart describes one embodiment of the present method. The method involves, at stage 310, selecting a target tissue 60. At stage 320, an energy delivery system 50 is selected for the target tissue 60. Stage 330 involves creating at least one hole 71 in the target tissue 60, whilst at stage 340, pressure is applied on the target tissue 60 to decrease the patency of the at least one hole 71. A material 110 is administered on target tissue 60 at stage 350, and finally at stage 360, the pressure on the target tissue 60 is released, allowing the at least one hole 71 to increase its patency and to suck the administered material 110 into the at least one hole 71.

Figure 4:
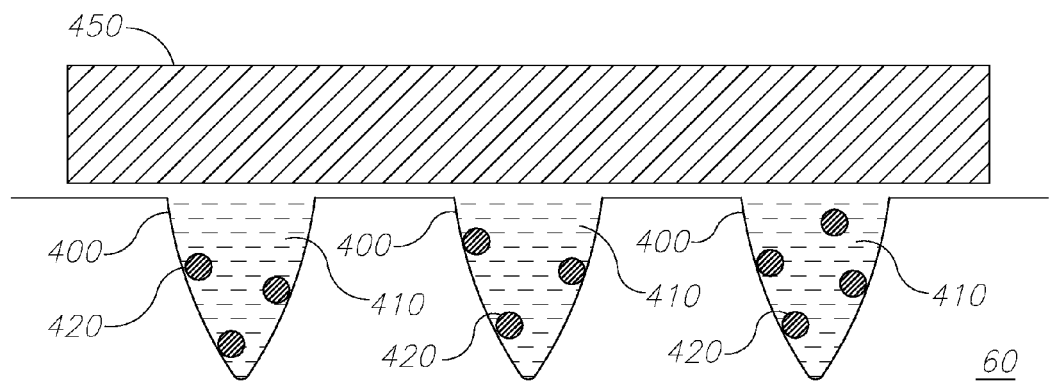
FIG. 4 illustrates one conceptual cavitation bubble management system.

Referring now to FIG. 4 which illustrates target tissue 60 and an array of holes 400 which are filled with fluid or material 410. The source of the fluid inside the holes may be internal or external. Interstitial fluid may diffuse into the hole through the hole wall as a result of the fractional treatment. In addition, fluid and therapeutic or cosmetic material may be administered onto the target tissue from the material/fluid reservoir. Administered material or fluid may be controlled by one or more methods of the present invention so that it will fill the hole volume.

In this embodiment of the present invention, (FIG. 5), a transducer 450 is in contact with the target tissue directly or through a coupling material. In one embodiment the coupling material is also administered from the material reservoir 90 through the dispensing element 91. The transducer 450 is configured to deliver ultrasound energy onto the target tissue and the fluid inside the holes 410 so that micro bubbles 420 are formed in the fluid 410. In one embodiment, the controller 30 is configured to monitor the micro bubbles 420 formation, distribution, density, size, growth rate and shrinking rate and cavitation through at least one acoustical sensor or at least one optical sensor. The sensors are configured to detect signals which are related to at least one of the following: bubble formation, bubble distribution, bubble density, bubble size, bubble growing pace, bubble shrinking pace and bubble cavitation. Sensors are coupled with their relevant energy sources to detect these related signals.

In one embodiment of the present invention, a light source probes the target tissue and an optical sensor is configured to detect at least one of the following changes which are related to the target tissue or the fluid inside the hole: changes in light absorption characteristics; backscattered light intensity changes; spectral changes; or reflection changes. In yet another embodiment of the present invention an ultrasonic transducer probes the target tissue and an ultrasonic sensor is configured to detect at least one of the following changes which are related to the target tissue or the fluid inside the hole: changes in reflected signals; changes in sound velocity; and changes in sound intensity. In yet another embodiment of the present invention RF electrodes are used to detect changes in the target tissue impedance or electrical conductivity.

Monitoring the bubble's dynamic characteristics by sensors and a processing unit serves as a feedback to the control unit 30 and transducer 450 is such a way that hole patency is controlled. The internal pressure inside the hole is increased by an increase in the average bubble size; bubble density or bubble distribution. This facilitates to overcome forces, such as pressure external to the hole, which tend to collapse the hole.

Figure 5:
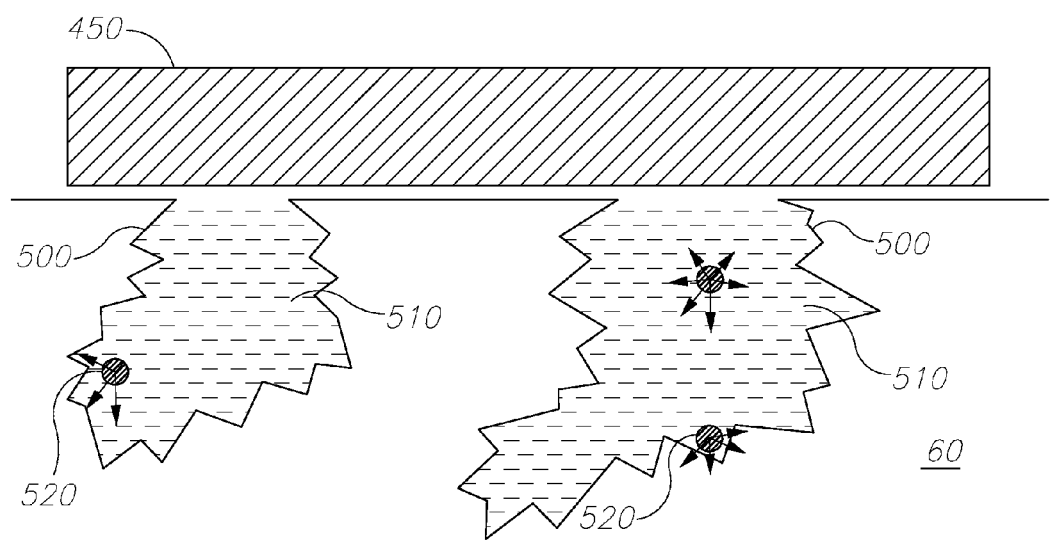
FIG. 5 illustrates hole fragmentation (ablation) through bubble cavitation.

FIG. 5 illustrates cavitation of bubbles in the fluid inside the hole, according to an embodiment of the present invention. Cavitation energy (where the bubbles implode or explode), facilitates further ablation and fragmentation of the hole from its internal volume and in a non-homogeneous way. As a result, the cavitation increases both hole volume and its internal surface area.

In yet another embodiment, when therapeutic or cosmetic material is delivered into the hole, an increased hole volume and internal surface area of the hole may increase bioavailability of the active material; increase its diffusion pace into the target tissue and/or more intensely activate healing response of the tissue.

The ultrasound transducer 450 may be configured to deliver ultrasound waves onto the tissue which are approximately perpendicular to the tissue surface, according to one embodiment of the present invention. In yet another embodiment, transducer 450 may deliver surface waves to the tissue which propagate in the tissue approximately parallel to the target tissue surface. In a further embodiment, the transducer 450 is located away from the target tissue and is configured to delivers energy through surface waves. In yet a further embodiment, the transducer 450 delivers ultrasound energy to cause the average bubble size to fluctuate so that the hole patency is pulsating. A pulsating hole patency increases fluid circulation inside and outside the hole and allows more efficient active material distribution and absorbance. This is highly desirable, particularly when therapeutic or cosmetic materials or fluids are dispensed onto the target tissue.

In another embodiment, an abrasive material is supplied into the hole from the material reservoir. The abrasive material per-se interacts with the ultrasound energy or with light energy causing the abrasive material to absorb more energy and explode toward the hole wall and therefore increase the ablation rate and hole growth. This increases the internal surface area of the micro hole, enabling more fluid to enter the hole, which may prove an advantage during the use of therapeutic or cosmetic fluids.

In the above description, an embodiment is an example or implementation of the invention. The various appearances of "one embodiment", "an embodiment" or "some embodiments" or "embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. A method of fractional treatment of tissue, said method comprising:
   creating at least one micro hole in a target tissue;
   administering material and/or fluid and/or drug onto said target tissue under sub-atmospheric pressure conditions, the patency of said at least one micro hole being decreased;
   increasing the sub-atmospheric pressure to above atmospheric conditions to thereby increase the patency of said at least one micro hole; and
   propelling said material and/or fluid/and/or drug into said at least one micro hole.

2. The method according to claim 1, wherein said material comprises an abrasive material.

3. The method according to claim 1, wherein said material and/or fluid comprises a cosmetic and/or therapeutic material and/or fluid.

4. The method according to claim 1, wherein said method further comprises removing excess fluid secreted by said target tissue.

5. The method according to claim 1, wherein said above atmospheric pressure is a positive pressure and wherein said pressure is applied approximately on top of said target tissue.

6. The method according to claim 5, wherein said application of said above atmospheric pressure is applied by the application of an adjustable mechanical grid on said target tissue.

7. The method according to claim 6, wherein said mechanical grid comprises at least a dimension x, a width dimension y and a micro hole spacing dimension z, wherein said patency of said at least one micro hole is changed by increasing or decreasing said at least one dimension of said grid.

8. The method according to claim 1, wherein said sub-atmospheric pressure is a negative pressure, and wherein said pressure is applied approximately on the sides of said target tissue.

9. A device for fractional treatment of tissue, said device comprising:
   an energy source,
   wherein said energy source is configured to create at least one micro hole in a target tissue;
   a pressure source,
   wherein said pressure source is configured to exert and release pressure on said target tissue,
   a reservoir,
   wherein said reservoir is configured to contain material and/or fluid and/or drug and controllably release said material and/or fluid and/or drug onto said target tissue; and
   a controller,
   wherein said controller is configured to activate said energy source to create at least one micro hole in said target tissue and to change the pressure over said target tissue, wherein the controller activates the reservoir and the pressure source so as to administer material and/or fluid and/or drug to said target tissue under sub-atmospheric pressure conditions, thus decreasing the patency of said at least one micro hole; and then to increase the sub-atmospheric pressure to above atmospheric pressure conditions to thereby increase the patency of the at least one micro hole.

10. The device according to claim 9, wherein said contained material and/or fluid comprises cosmetic material and/or fluid.

11. The device according to claim 9, wherein said pressure source is configured to produce positive and negative pressure.

12. The device according to claim 9, wherein said controller is configured to change the pressure over said target tissue.

13. The device according to claim 9, further comprising an excess fluid removal means.

14. A device according to claim 9, further comprising:
   an adjustable grid having at least a length dimension x, a width dimension y and a spacing dimension z said grid being provided with holes to create micro holes in said target tissue, in conjunction with said energy source;

wherein said grid is configured to be placed on said target tissue;

an adjusting mechanism configured to change at least one dimension of said grid;

wherein an adjustment of at least one dimension of said grid is configured to change the hole size dimension of said holes to increase or decrease the patency of said micro holes.

15. The device according to claim 14, wherein said grid is rigid.

16. The device according to claim 14, wherein said grid is configured to be placed on said target tissue by a sticker.

* * * * *